(12) United States Patent
Sakurai et al.

(10) Patent No.: US 10,613,310 B2
(45) Date of Patent: Apr. 7, 2020

(54) OBSERVATION DEVICE AND OBSERVATION METHOD

(71) Applicant: OLYMPUS CORPORATION, Tokyo (JP)

(72) Inventors: Ayumu Sakurai, Tokyo (JP); Mina Kobayashi, Tokyo (JP); Toshiyuki Hattori, Tokyo (JP); Naohiro Ariga, Tokyo (JP); Takashi Miyoshi, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 180 days.

(21) Appl. No.: 15/959,610

(22) Filed: Apr. 23, 2018

(65) Prior Publication Data

US 2018/0314046 A1 Nov. 1, 2018

(30) Foreign Application Priority Data

Apr. 27, 2017 (JP) ................... 2017-088197

(51) Int. Cl.
*G02B 21/08* (2006.01)
*C12M 1/34* (2006.01)
(Continued)

(52) U.S. Cl.
CPC ............. *G02B 21/084* (2013.01); *C12M 1/34* (2013.01); *G02B 21/06* (2013.01); *G02B 21/14* (2013.01);
(Continued)

(58) Field of Classification Search
CPC ...... G02B 21/084; G02B 21/14; G02B 21/26; G02B 21/361; G02B 21/365; C12M 1/34
See application file for complete search history.

(56) References Cited

U.S. PATENT DOCUMENTS

| | | | |
|---|---|---|---|
| 4,561,731 A | 12/1985 | Kley | |
| 2012/0057013 A1* | 3/2012 | Ishiwata | G02B 21/367 348/78 |

(Continued)

FOREIGN PATENT DOCUMENTS

| | | |
|---|---|---|
| EP | 3 009 500 A1 | 4/2016 |
| EP | 3211469 A1 | 8/2017 |

(Continued)

OTHER PUBLICATIONS

Extended European Search Report dated Oct. 2, 2018 in European Patent Application No. 18 16 8666.8.

*Primary Examiner* — Wen Huang
(74) *Attorney, Agent, or Firm* — Scully, Scott, Murphy & Presser, P.C.

(57) ABSTRACT

An observation device including: an imaging element that captures images of cells contained in a culture vessel; an oblique illumination device that performs oblique illumination to the cells from a plurality of illumination directions, out of the optical axis of the imaging element; a controller that detects the relationship between the position of the culture vessel and the position of the imaging element and that selects the illumination directions of the oblique illumination device on the basis of the detected relationship between the position of the culture vessel and the position of the imaging element; and an image processor that applies, on the basis of the illumination direction of the oblique illumination device, processing for reducing shadows on the cells caused by the oblique illumination, to an image of the cells acquired by the imaging element.

15 Claims, 8 Drawing Sheets

(51) Int. Cl.
  *G02B 21/36*  (2006.01)
  *G02B 21/26*  (2006.01)
  *G02B 21/14*  (2006.01)
  *G02B 21/06*  (2006.01)
  *G06T 5/00*  (2006.01)

(52) U.S. Cl.
  CPC .......... *G02B 21/26* (2013.01); *G02B 21/361* (2013.01); *G02B 21/365* (2013.01); *G06T 5/008* (2013.01); *G06T 2207/10056* (2013.01); *G06T 2207/30024* (2013.01)

(56) References Cited

U.S. PATENT DOCUMENTS

| | | |
|---|---|---|
| 2016/0108353 A1 | 4/2016 | Kimura |
| 2017/0261732 A1 | 9/2017 | Takahashi et al. |
| 2018/0045935 A1 | 2/2018 | Aoki |

FOREIGN PATENT DOCUMENTS

| | | |
|---|---|---|
| EP | 3 284 814 A1 | 2/2018 |
| JP | 2016-077226 A | 5/2016 |
| JP | 2018-025627 A | 2/2018 |
| JP | 2018-072845 A | 5/2018 |
| WO | WO 2016/158780 A1 | 10/2016 |

\* cited by examiner

OBSERVATION DEVICE AND OBSERVATION METHOD

CROSS-REFERENCE TO RELATED APPLICATIONS

This application is based on and claims priority to Japanese Patent Application No. 2017-088197 filed on Apr. 27, 2017, the content of which is incorporated herein by reference in its entirety.

Technical Field

The present invention relates to an observation device and an observation method.

Background Art

In the related art, there is a known observation device in which cells in culture are subjected to oblique illumination, and an image of the cells is acquired (for example, see PTL 1). In the observation device described in PTL 1, a plurality of LED light sources are disposed, below a vessel, around an objective lens, illumination light emitted from each of the LED light sources is reflected at a top plate disposed above the vessel, thus illuminating the cells obliquely from above, and the LED light sources to be turned on are switched, thereby allowing oblique illumination from different directions.

CITATION LIST

Patent Literature

{PTL 1} PCT International Publication No. WO 2016/158780

SUMMARY OF INVENTION

According to a first aspect, the present disclosure provides an observation device including: an imaging unit configured to capture an image of a specimen contained in a vessel; an oblique illumination unit configured to perform an oblique illumination of the specimen from a plurality of illumination directions outside an optical axis of the imaging unit; a relative-position detector configured to detect a relationship between a position of the vessel and a position of the imaging unit; an illumination-direction switching unit configured to select a illumination direction to illuminate the specimen among the illumination directions of the oblique illumination unit on the basis of the relationship between the position of the vessel and the position of the imaging unit, which is detected by the relative-position detector; and an image processor configured to apply, on the basis of the illumination direction selected by the illumination-direction switching unit, image processing for reducing a shadow on the specimen caused by the oblique illumination, to an image of the specimen acquired by the imaging unit.

According to a second aspect, the present disclosure provides an observation method comprising: a switching step of selecting a illumination direction to apply oblique illumination to a specimen among illumination directions on the basis of a relationship between a position of a vessel that contains the specimen and a position of an imaging unit that captures an image of the specimen in the vessel; an illumination step of applying the oblique illumination to the specimen from the illumination direction selected in the switching step; an image-capturing step of capturing, by means of an imaging unit, an image of the specimen to which the oblique illumination is applied by the illumination step; and an image processing step of applying, on the basis of the illumination direction selected by the switching step, image processing for reducing a shadow on the specimen caused by the oblique illumination, to an image of the specimen acquired by the imaging unit.

DESCRIPTION OF EMBODIMENTS

An observation device and an observation method according to one embodiment of the present invention will be described below with reference to the drawings.

Figure 1:
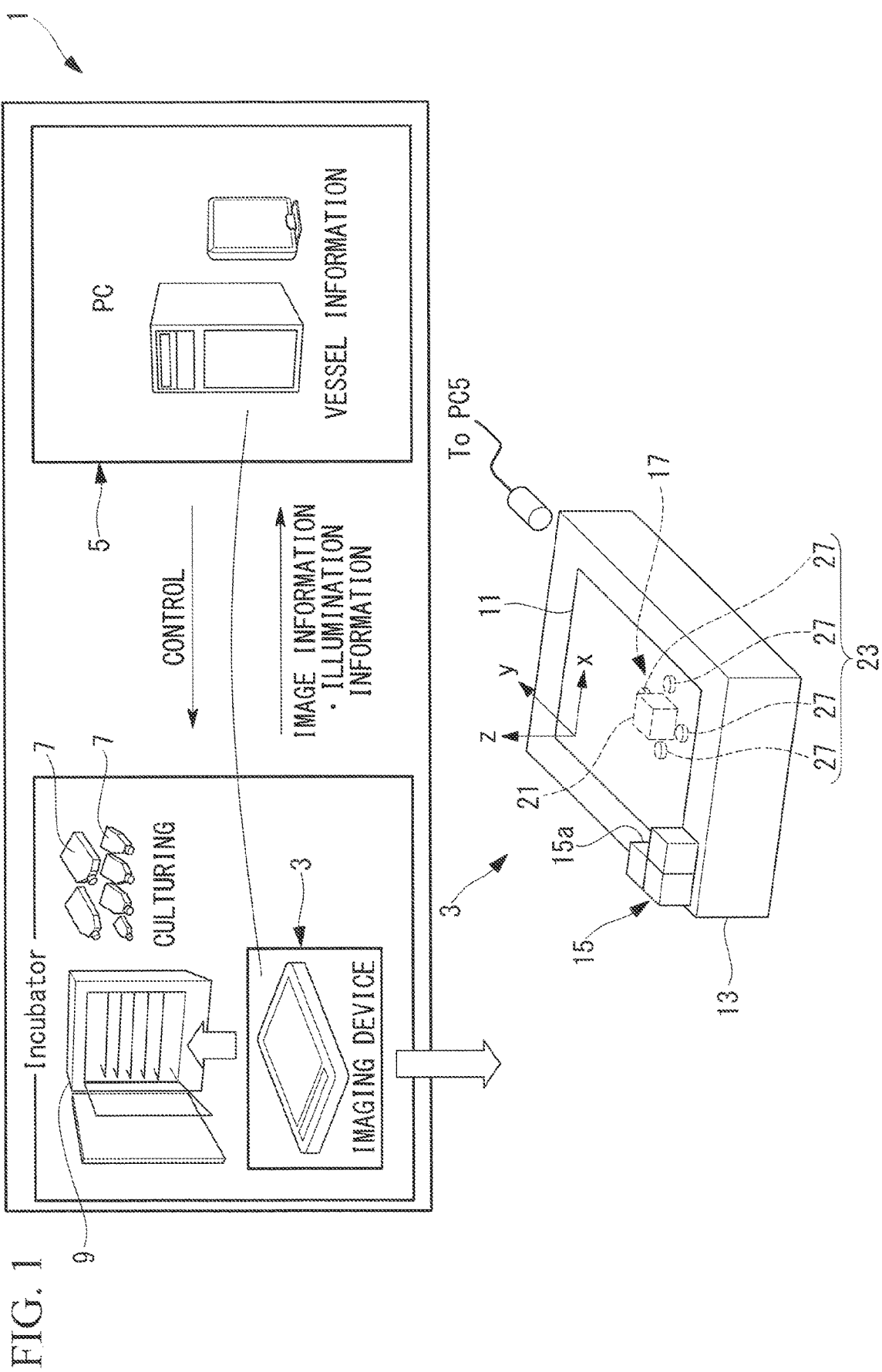
FIG. 1 is a schematic configuration diagram of an observation device according to one embodiment of the present invention.
Figure 2:
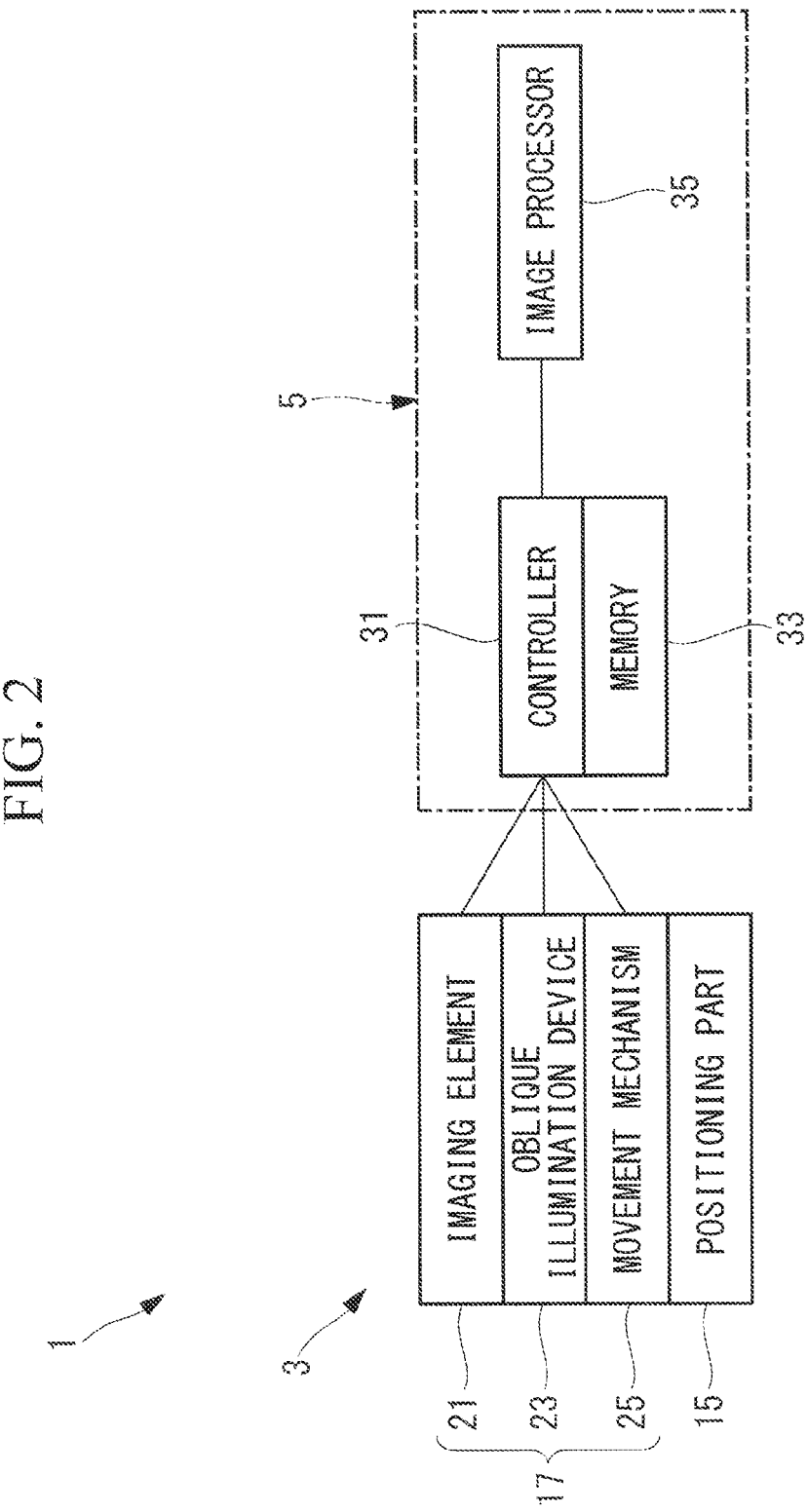
FIG. 2 is a block diagram showing the observation device shown in FIG. 1.

As shown in FIGS. 1 and 2, an observation device 1 of this embodiment is provided with an imaging device 3 that acquires an image of cells (specimen, not shown) and a PC (personal computer) 5 that performs control of the imaging device 3 and storage, processing, etc., of image information.

The imaging device 3 is provided with: a housing 13 that has an optically-transparent glass plate 11 on which a culture vessel (vessel) 7 containing cells is mounted; a positioning part 15 against which the culture vessel 7 is made to abut, on the glass plate 11, thus being positioned; and an imaging unit 17 that is disposed, in the housing 13, below the glass plate 11 and that captures images of the cells in the culture vessel 7.

The culture vessel 7 is a cell culture flask having a top plate, for example, and is formed entirely of optically transparent resin. The cells are contained in the culture vessel 7, are put in an incubator 9, and are cultured in the incubator 9.

The glass plate 11 is formed in a rectangular shape, for example, and is disposed on the upper surface of the housing 13. For example, the lateral direction of the glass plate 11 is defined as the X-direction, the longitudinal direction thereof is defined as the Y-direction, and the thickness direction of the glass plate 11 is defined as the Z-direction.

The positioning part 15 has abutment surfaces 15a that are provided at, for example, one of the corner sections of the glass plate 11, that rise in the Z-direction, and that extend in the X-direction and the Y-direction. At the positioning part 15, the culture vessel 7 can be positioned in the X-direction and the Y-direction when the culture vessel 7 mounted on the glass plate 11 is made to abut against the abutment surfaces 15a. Therefore, the position of the culture vessel 7 is fixed by means of the positioning part 15.

The imaging unit 17 is provided with: an imaging element (imaging unit) 21 that receives light coming from the cells and transmitted through the glass plate 11 to capture an image of the cells; an oblique illumination device (oblique illumination unit) 23 that emits illumination light upward through the glass plate 11; and a movement mechanism 25 that integrally moves, below the glass plate 11, the imaging element 21 and the oblique illumination device 23 in directions that intersect with an imaging optical axis.

The imaging element 21 has the imaging optical axis extending along the Z-direction and is disposed so as to be opposed to the glass plate 11. Image information of the cells acquired by the imaging element 21 is sent to the PC 5.

Figure 3:
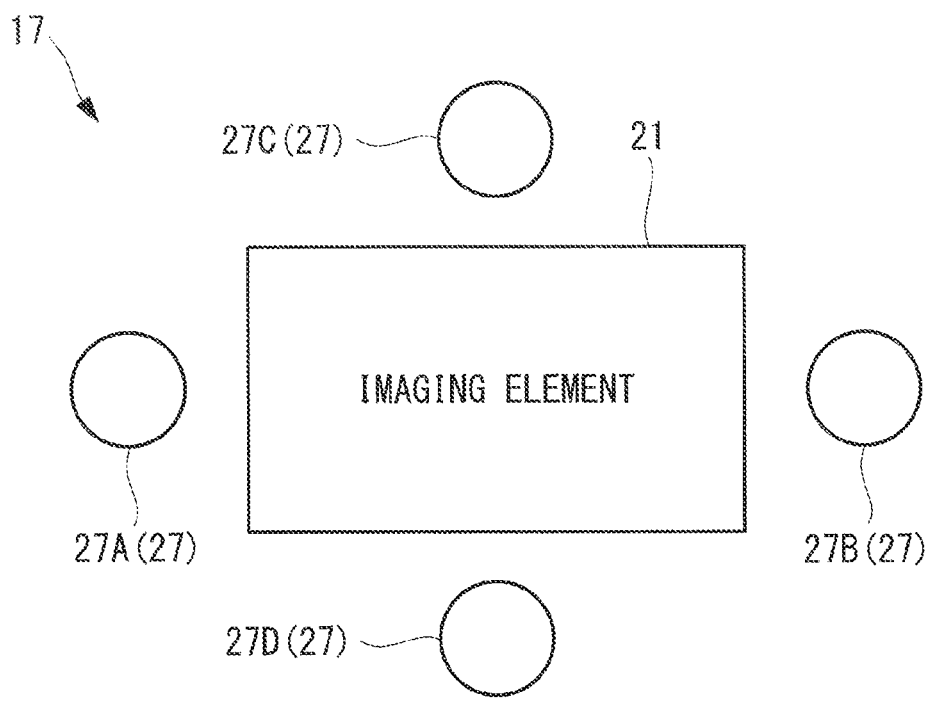
FIG. 3 is a plan view of an example arrangement of LED light sources, viewed in the direction along an imaging optical axis.

As shown in FIG. 3, the oblique illumination device 23 is provided with a plurality of (in this embodiment, four) LED light sources 27 (hereinafter, also individually referred to as LED light source 27A, LED light source 27B, LED light source 27C, and LED light source 27D) that are disposed around the imaging element 21 at even intervals in the circumferential direction. Two of the four LED light sources 27 are disposed spaced apart from each other in the X-direction with the imaging element 21 therebetween, and the other two thereof are disposed spaced apart from each other in the Y-direction with the imaging element 21 therebetween.

Each of the LED light sources 27 emits illumination light obliquely upward from below the glass plate 11, causes the illumination light to be transmitted through the glass plate 11 and the bottom surface of the culture vessel 7, and causes the illumination light to be reflected at the top plate of the culture vessel 7, thus radiating the illumination light onto the cells obliquely from above. The oblique illumination device 23 can independently turn on each of the LED light sources 27.

As shown in FIG. 2, the PC 5 is provided with: a controller (relative-position detector, illumination-direction switching unit, light-intensity adjuster) 31 that performs various settings in response to inputs from a user and that controls the imaging unit 17; a memory 33 that stores vessel information and image information; and an image processor 35 that processes an image of cells acquired by the imaging device 3.

The controller 31 reads position information of the imaging element 21 from the movement mechanism 25. Furthermore, the controller 31 detects the relationship (relative position) between the position of the imaging element 21 and the position of the culture vessel 7, which is positioned by the positioning part 15, on the basis of the position information from the movement mechanism 25.

Figure 4:
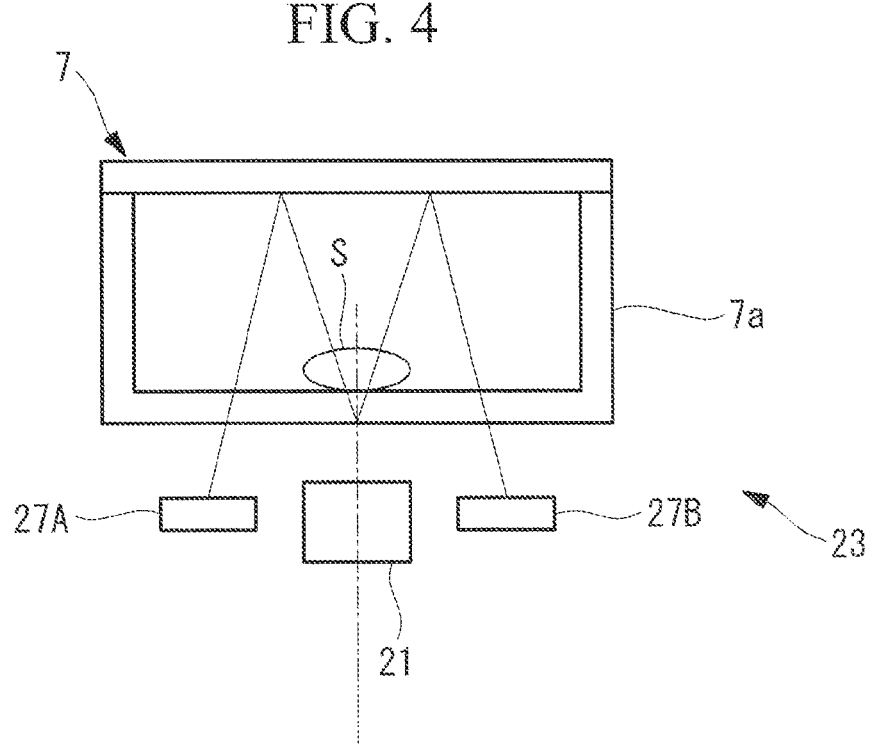
FIG. 4 is a diagram showing an example illumination direction when the center of a culture vessel is observed.
Figure 5:
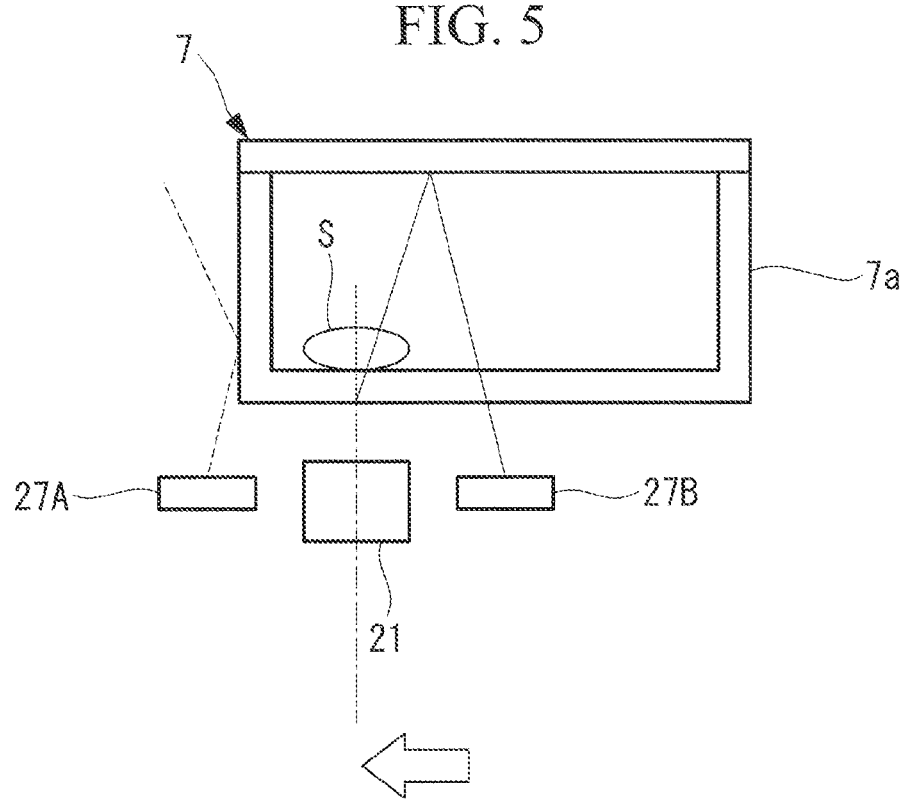
FIG. 5 is a diagram showing an example illumination direction when a left end of the culture vessel is observed.
Figure 6:
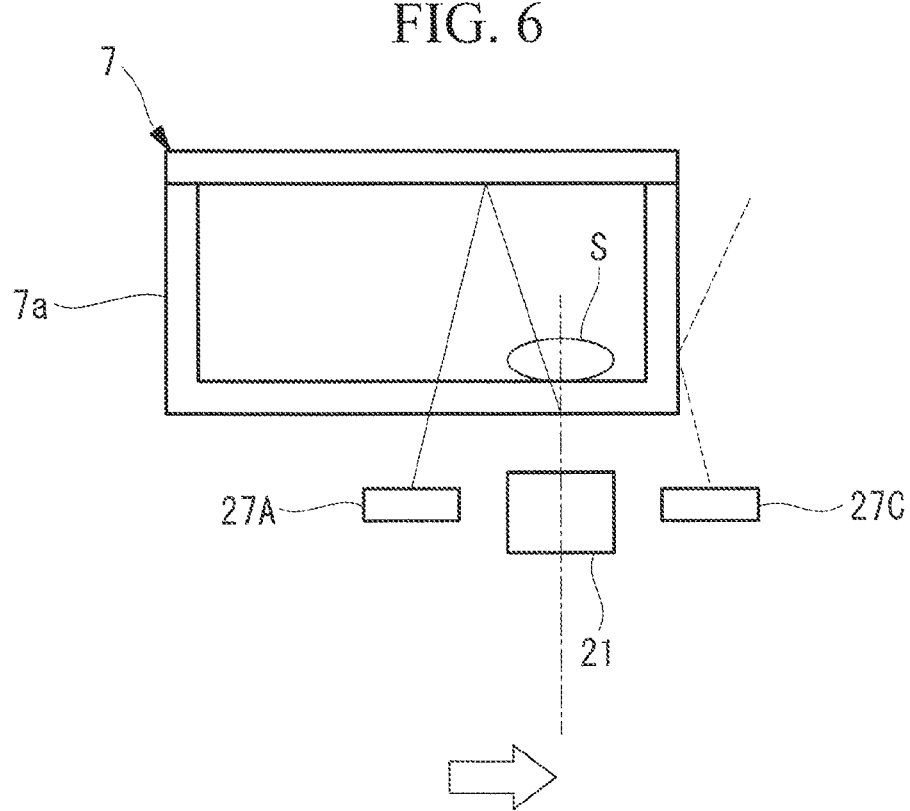
FIG. 6 is a diagram showing an example illumination direction when a right end of the culture vessel is observed.

Furthermore, the controller 31 switches between the illumination directions of the oblique illumination device 23 on the basis of the detected relationship between the position of the culture vessel 7 and the position of the imaging element 21, and the shape of the culture vessel 7 stored in the memory 33, so as to prevent illumination light from passing through a peripheral edge 7a of the culture vessel 7, for example (see FIGS. 4 to 6). For example, when straight lines are extended from the center of the imaging element 21 toward the respective LED light sources 27, the controller 31 selects and turns on the LED light source 27 by selecting the LED light source 27 which has the longest distance from the peripheral edge 7a of the culture vessel 7 in the extension direction of each straight line.

More specifically, as shown in FIG. 4, when the center of the culture vessel 7 is to be observed, whichever one of the LED light sources 27A, 27B, 27C, and 27D is turned on, illumination light is not blocked (any of the LED light sources 27 can be turned on). When the imaging element 21 and the four LED light sources 27 are moved by the movement mechanism 25, and a left end of the culture vessel 7 (side closer to the left side than the center of the culture vessel 7 is, with respect to the plane of FIG. 5) or a right end of the culture vessel 7 (side closer to the right side than the center of the culture vessel 7 is, with respect to the plane of FIG. 6) is to be observed, illumination light emitted from the LED light source 27 that is close to the peripheral edge 7a of the culture vessel 7 is blocked by the peripheral edge 7a of the culture vessel 7. In FIGS. 4 to 6, reference sign S denotes an observation position.

In this embodiment, in the case of FIG. 5 in which the left end of the culture vessel 7 is observed, the controller 31 turns on the LED light source 27B that is located on the right side with respect to the plane of FIG. 5, and, in the case of FIG. 6 in which the right end of the culture vessel 7 is observed, the controller 31 turns on the LED light source 27A that is located on the left side with respect to the plane of FIG. 6. Furthermore, in a case in which a rear side of the culture vessel 7 in the plane of FIG. 4 is observed, the controller 31 similarly turns on the LED light source 27D, shown in FIG. 3, and, in a case in which a front side of the culture vessel 7 in the plane of FIG. 4 is observed, the controller 31 turns on the LED light source 27C, shown in FIG. 3. By doing so, it is possible to perform appropriate oblique illumination without illumination light being blocked by the peripheral edge 7a of the culture vessel 7. The position information of the LED light source 27 that is turned on by the controller 31 is sent to the image processor 35 as information about the illumination direction of the oblique illumination device 23.

The image processor 35 applies processing for reducing the shadows on cells caused by oblique illumination, to an image of the cells acquired by the imaging element 21, on the basis of the information about the illumination direction of the oblique illumination device 23, which is sent from the controller 31.

Figure 7:
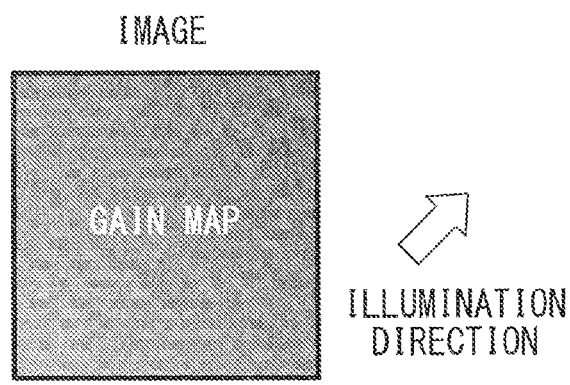
FIG. 7 is a diagram showing an example gain map.
Figure 8:
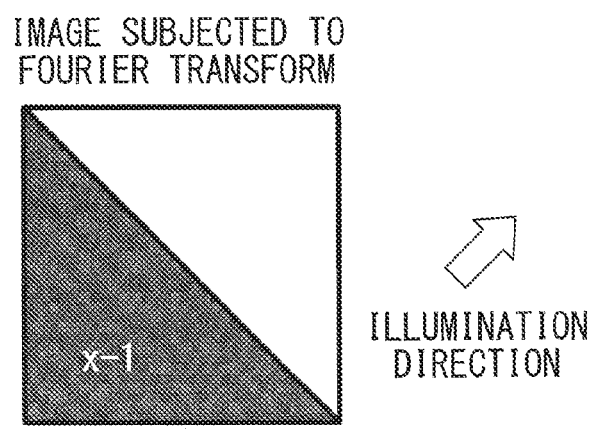
FIG. 8 is a diagram explaining processing of multiplication, by −1, an image that has been subjected to a Fourier transform.
Figure 9:
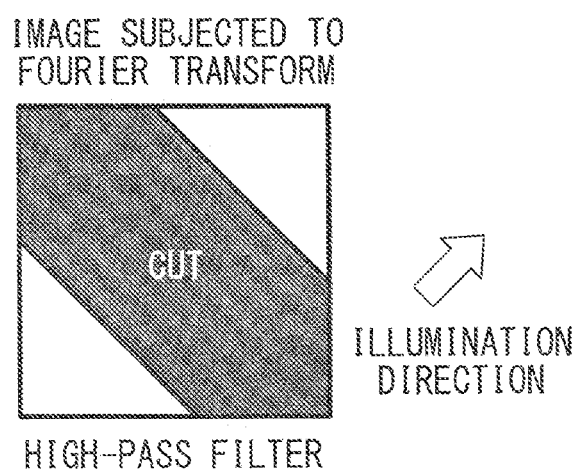
FIG. 9 is a diagram explaining processing for applying a high-pass filter to the image that has been subjected to the Fourier transform.

Specifically, the image processor 35 creates a gain map, such as that shown in FIG. 7, that is composed of gain values that are smaller on a nearer side and are larger on a farther side along the illumination direction with respect to the cells and multiplies the image of the cells by the gain values on the basis of the created gain map. Furthermore, the image processor 35 applies a Fourier transform to the image of the cells and multiplies, by −1, a region (hatched region in FIG. 8) in the image that has been subjected to the Fourier transform, the region including frequency components for the shadows, among frequencies along the illumination direction with respect to the cells, as shown in FIG. 8. Then, as shown in FIG. 9, the image processor 35 applies a high-pass filter to the image that has been subjected to the Fourier transform and then applies an inverse Fourier transform to the image of the cells.

Figure 10:
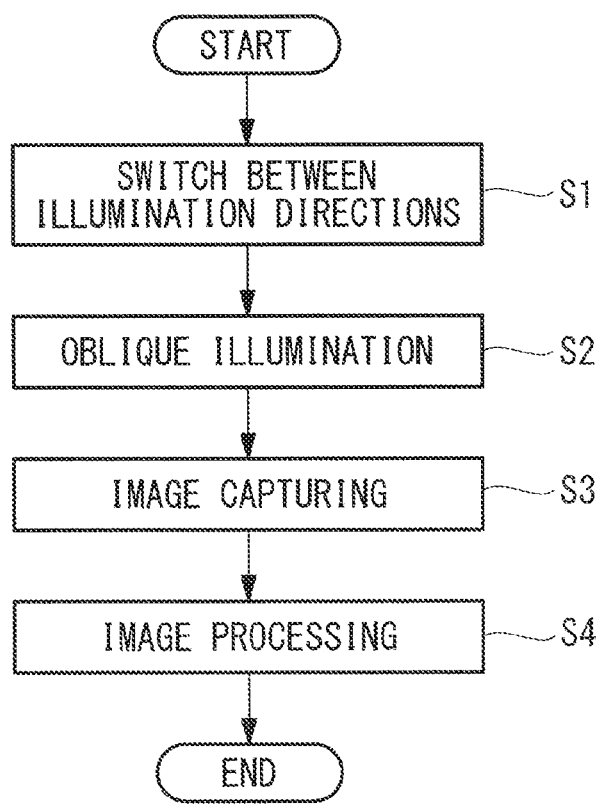
FIG. 10 is a flowchart for explaining an observation method according to an embodiment of the present invention.

Furthermore, as shown in the flowchart of FIG. 10, an observation method according to this embodiment includes: a switching step S1 of selecting a illumination direction to apply oblique illumination to cells on the basis of the relationship between the position of the culture vessel 7, which contains the cells, and the position of the imaging element 21, which captures images of the cells in the culture vessel 7; an illumination step S2 of applying oblique illumination to the cells S from the illumination direction selected in the switching step S1; an image-capturing step S3 of capturing, by means of the imaging element 21, images of the cells to which oblique illumination has been applied in the illumination step S2; and an image processing step S4 of applying processing for reducing the shadows on the cells caused by oblique illumination to the image of the cells acquired by the imaging element 21, on the basis of the illumination direction of oblique illumination.

The operation of the thus-configured observation device 1 and observation method will now be described.

In order to observe cells by using the observation device 1 of this embodiment, first, a user mounts the culture vessel 7, which contains cells, on the glass plate 11 of the imaging device 3 and causes the culture vessel 7 to abut against the positioning part 15, to position the culture vessel 7. Accordingly, the culture vessel 7 is set at a predetermined fixed position. Then, the user sets a plurality of image-capturing positions in the culture vessel 7 by means of the PC 5. Furthermore, the movement mechanism 25 adjusts the positions of the imaging element 21 and the oblique illumination device 23.

When the user sets the image-capturing positions, the controller 31 reads position information of the imaging element 21 from the movement mechanism 25 and detects the relationship between the position of the culture vessel 7 and the position of the imaging element 21. Then, on the basis of the detected relationship between the position of the culture vessel 7 and the position of the imaging element 21, and the shape of the culture vessel 7, for example, when straight lines are extended from the center of the imaging element 21 toward the respective LED light sources 27, the controller 31 selects and turns on the LED light source 27 by selecting the LED light source 27 which has the longest distance from the peripheral portion 7a of the culture vessel 7 in the extension direction of each straight line. (switching step S1).

Illumination light emitted obliquely upward from the LED light source 27 that is selected by the controller 31 is transmitted through the glass plate 11 and the bottom surface of the culture vessel 7 upward from below, is reflected at the top plate of the culture vessel 7, and is radiated on the cells obliquely from above (illumination step S2).

Of the illumination light that has been radiated onto the cells, transmitted light of the illumination light that has been transmitted through the cells is transmitted through the bottom surface of the culture vessel 7 and the glass plate 11 downward from above and is received by the imaging element 21. At this time, the illumination light is refracted and scattered due to the shapes of the cells and the refractive indices thereof or is dimmed due to the transmittance of the cells, thus turning into transmitted light containing information about the cells, and the transmitted light is image-captured by the imaging element 21 (image-capturing step S3).

Image information of the cells, acquired by the imaging element 21, is associated with the information about the illumination direction of the oblique illumination device 23, which is sent from the controller 31, and is sent to the image processor 35.

Then, the image processor 35 creates a gain map for shading correction, such as that shown in FIG. 7, that is composed of gain values that are smaller on a nearer side and are larger on a farther side along the illumination direction with respect to the cells, on the basis of the information about the illumination direction of the oblique illumination device 23, which is sent from the controller 31. Then, the image processor 35 multiplies the image of the cells by the gain values on the basis of the created gain map for shading correction (image processing step S4). Accordingly, it is possible to suppress shading that is caused on the image according to the illumination direction.

Next, the image processor 35 applies a Fourier transform to the image of the cells, and, as shown in FIG. 8, multiplies, by −1, a region in the image that has been subjected to the Fourier transform, the region including frequency components for the shadows, among frequencies along the illumination direction with respect to the cells (image processing step S4). Accordingly, it is possible to shift the phases of frequencies along the illumination direction in the image of the cells. In this case, high-frequency components for the edges etc. of the cells change little in appearance, thus remaining the same, and medium-frequency components for the shadows etc. of the cells change a lot in appearance, thus decreasing. Therefore, it is possible to efficiently reduce the shadows on the cells caused by oblique illumination.

Then, as shown in FIG. 9, the image processor 35 applies a high-pass filter to the image of the cells that has been subjected to the Fourier transform and then applies an inverse Fourier transform thereto (image processing step S4). Accordingly, it is possible to remove low-frequency components for portions where color changes less, other than the edges and the shadows on the cells, in the image that has been subjected to the Fourier transform. Therefore, through the processing for multiplying, by −1, a partial region of the image that has been subjected to the Fourier transform, it is possible to reduce a striped pattern caused at the low-frequency components, thus improving the image quality.

The image of the cells that has been subjected to the image processing by the image processor 35 is stored in the memory 33.

As described above, according to the observation device 1 of this embodiment, the illumination directions are switched on the basis of the relationship between the position of the culture vessel 7 and the position of the imaging element 21, and the cells in the culture vessel 7 are subjected to oblique illumination, thereby making it possible to prevent illumination for the cells from being blocked according to the position, the shape, etc., of the culture vessel 7 and to efficiently apply oblique illumination to the cells.

In this case, although shadows are cast on the cells in different ways according to the illumination directions, and, when the directions of oblique illumination are switched, the shapes of the cells in the image change, the image processor 35 applies, on the basis of the illumination direction, processing for reducing the shadows on the cells caused by oblique illumination to the image of the cells, thereby making it possible to suppress a change in the shapes of the cells between images in which the illumination directions differ. Therefore, it is possible to acquire an image from which a stable analysis result of cells can be obtained irrespective of the direction of oblique illumination.

In this embodiment, although the controller 31 selects the LED light source 27 to be turned on, thus switching between the illumination directions of the oblique illumination device 23, it is also possible to, while keeping the plurality of LED light sources 27 turned on, switch between an increase and a decrease in the light intensities thereof, thus switching between the illumination directions of the oblique illumination device 23.

Furthermore, this embodiment can be modified as follows.

In a first modification, it is possible to adopt a position-information input unit with which the user inputs position information of the culture vessel 7.

In this case, for example, the PC 5 may be provided with the position-information input unit, such as a mouse and a keyboard, and the user may input the position information of the culture vessel 7 on the glass plate 11 of the imaging device 3, by means of the position-information input unit of the PC 5.

By doing so, the position information of the culture vessel 7 input by the user can be used as is as the position of the culture vessel 7.

In a second modification, the imaging device 3 may be provided with: instead of the glass plate 11, as the relative-position detector, a stage on which the culture vessel 7 is mounted; a stage movement mechanism that moves the stage at least in directions intersecting with the imaging optical axis of the imaging element 21; and a stage-position detector that detects the position of the stage on the basis of the amount of movement of the stage moved by the stage movement mechanism (all of which are not shown). In this case, the positioning part 15 positions the culture vessel 7 on the stage.

By doing so, the position of the stage can be easily found on the basis of the amount of movement thereof moved by the stage movement mechanism, and the culture vessel 7 positioned on the stage by the positioning part 15 is moved integrally with the stage. Therefore, on the basis of the position of the stage detected by the stage-position detector, the controller 31 can easily detect the relationship (relative position) between the position of the imaging element (imaging unit) 21 and the position of the culture vessel 7.

In a third modification, a mark may be made in advance on the culture vessel 7, and the imaging device 3 may be provided with, as the relative-position detector, a sensor (not shown) that reads the predetermined mark, which is made on the culture vessel 7, to detect the position of the mark.

By doing so, the entire culture vessel 7 need not be detected, and the sensor can easily detect the position of the culture vessel 7 merely by detecting the mark. Therefore, the controller 31 can easily detect the relationship (relative position) between the position of the imaging element (imaging unit) 21 and the position of the culture vessel 7 on the basis of the position of the mark detected by the sensor.

In a fourth modification, the imaging device 3 may be provided with: as the relative-position detector, a camera that captures an image of the entire culture vessel 7; and an image analyzer that analyzes an image of the culture vessel 7 acquired by the camera (all of which are not shown).

By doing so, it is possible to easily and accurately detect the position of the culture vessel 7 from information obtained when the image analyzer analyzes the image of the entire culture vessel 7. Therefore, on the basis of the analysis result of the image of the culture vessel 7 obtained by the image analyzer, the controller 31 can easily detect the relationship (relative position) between the position of the imaging element (imaging unit) 21 and the position of the culture vessel 7.

In a fifth modification, the imaging device 3 may be provided with, instead of the glass plate 11, as the relative-position detector, a touch panel (vessel placement unit) on which the culture vessel 7 is placed; and a sensor that senses, by weight or the like, the position on the touch panel with which the culture vessel 7 is brought into contact (all of which are not shown).

By doing so, the sensor merely senses the position on the touch panel with which the culture vessel 7 is brought into contact, thereby making it possible to easily and accurately detect the position of the culture vessel 7. Therefore, on the basis of the position with which the culture vessel 7 is brought into contact, sensed by the sensor, the controller 31 can easily detect the relationship (relative position) between the position of the imaging element (imaging unit) 21 and the position of the culture vessel 7.

Furthermore, in the above-described embodiment, although the four LED light sources 27 are disposed around the imaging element 21, instead of this, the arrangement thereof can be modified as follows.

Figure 11:
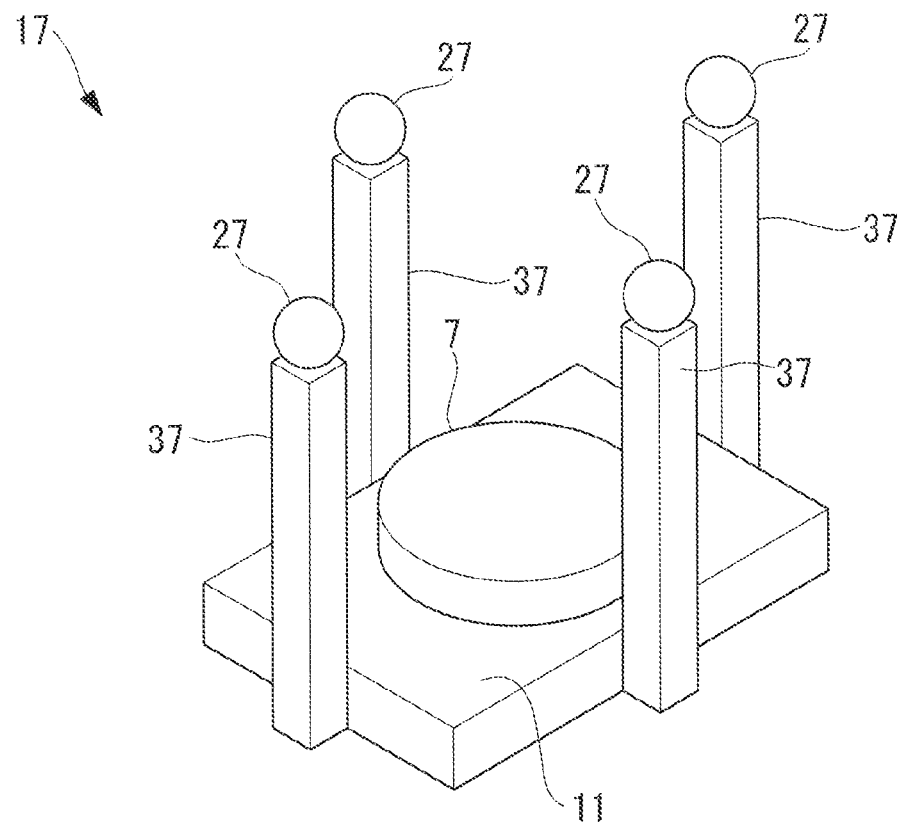
FIG. 11 is a perspective view showing the configuration of a modification of the present invention in which a plurality of LED light sources are disposed at positions obliquely above a culture vessel.

In a sixth modification, for example, as shown in FIG. 11, a plurality of (in the example shown in FIG. 11, four) LED light sources 27 may be disposed at intervals in the circumferential direction at positions obliquely above the glass plate 11, with the imaging element 21 being disposed below the glass plate 11.

In this case, as shown in FIG. 11, it is also possible to dispose, around the glass plate 11, a plurality of support posts 37 that extend in the vertical direction and to support, by means of the support posts 37, the respective LED light sources 27 at positions obliquely above the culture vessel 7.

With this configuration, illumination light can be radiated obliquely from above onto the cells in the culture vessel 7, without causing the illumination light to be transmitted through the glass plate 11. Accordingly, it is possible to avoid loss of the light intensity of illumination light caused when the illumination light is transmitted through the glass plate 11.

Figure 12:
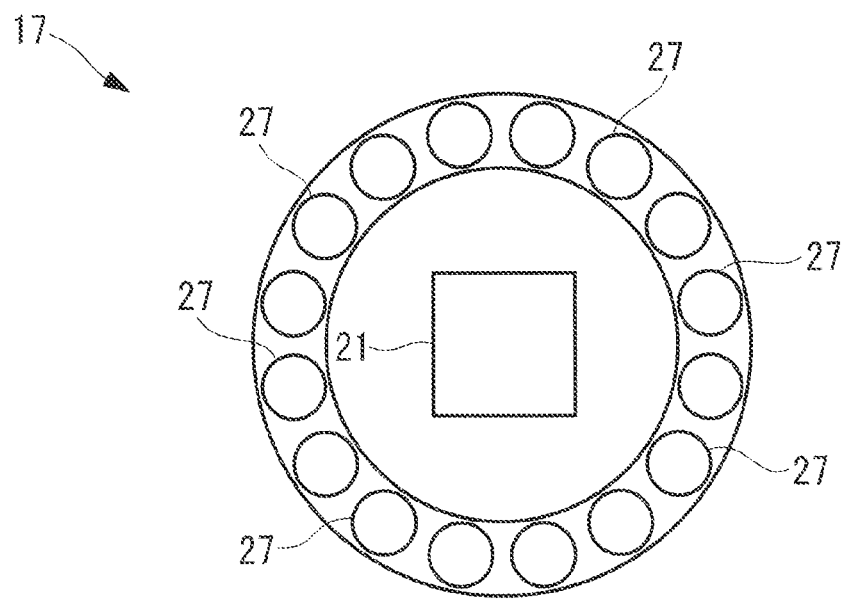
FIG. 12 is a plan view of the configuration of a modification of the present invention in which a plurality of LED light sources are arranged in the form of a ring, viewed from the direction along the imaging optical axis.

In a seventh modification, for example, as shown in FIG. 12, a plurality of (16 in the example shown in FIG. 12) LED light sources 27 may also be arranged in the form of a ring around the imaging element 21. In this case, it is also possible to dispose, together with the imaging element 21, the respective LED light sources 27 below the glass plate 11, or it is also possible to dispose the imaging element 21 below the glass plate 11 and to dispose the respective LED light sources 27 at positions obliquely above the glass plate 11.

By doing so, the positions, in the circumferential direction, of the LED light sources 27 that are made to perform illumination are switched, thereby making it possible to capture images of the cells illuminated from different directions in the circumferential direction.

In an eighth modification, a plurality of LED light sources 27 may also be disposed around the imaging element 21 at different positions in the radial direction from the optical axis of the imaging unit.

By doing so, the positions, in the radial directions, of the LED light sources 27 that are made to perform illumination are switched, thereby making it possible to capture images of the cells illuminated from different angles in the direction along the imaging optical axis of the imaging element 21.

Specifically, the cells can be subjected to oblique illumination at a small angle with respect to the imaging optical axis, from the LED light source 27 that is disposed close to the imaging optical axis in the radial direction, whereas the cells can be subjected to oblique illumination at a large angle with respect to the imaging optical axis, from the LED light source 27 that is disposed away from the imaging optical axis in the radial direction.

Figure 13:
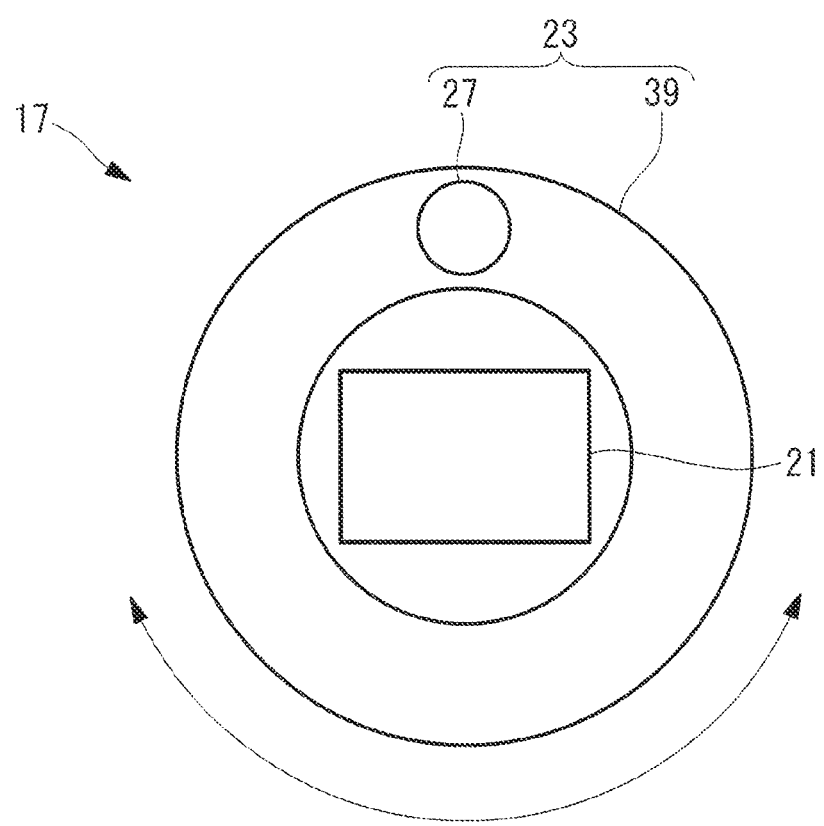
FIG. 13 is a plan view of the configuration of a modification of the present invention in which an LED light source and an imaging element are disposed in a movable manner around a predetermined rotational axis, viewed from the direction along the imaging optical axis.

In a ninth modification, for example, as shown in FIG. 13, the oblique illumination device 23 may be provided with: an LED light source 27 that can be moved in a direction intersecting with the imaging optical axis of the imaging element 21; and a light-source movement mechanism that moves the LED light source 27.

In this case, it is possible to adopt, as the light-source movement mechanism, a turret 39, such as that shown in FIG. 13, that is rotatable about a predetermined rotational axis extending along the imaging optical axis of the imaging element 21. Then, the LED light source 27 may be attached to the turret 39, and the turret 39 may be rotated, thereby causing the LED light source 27 to move in the circumferential direction around the imaging element 21.

By doing so, the position of the LED light source 27 is changed by the turret 39, thereby making it possible to switch between the illumination directions, with a small number of LED light sources 27, and to subject the cells to oblique illumination.

Furthermore, in a tenth modification, the observation device 1 may be provided with: as the relative-position detector, an imaging unit movement mechanism on which the imaging element 21 is mounted and that can be moved in at least a direction intersecting with the imaging optical axis of the imaging element 21; and an imaging unit position detector that detects the position of the imaging element 21 on the basis of position information of the imaging unit movement mechanism (all of which are not shown).

By doing so, the imaging unit movement mechanism can change the position of the imaging element 21 in accordance with the position and the shape of the culture vessel 7 and the positions of the cells in the culture vessel 7 and can reliably capture images of the desired cells. In this case, even when the imaging element 21 is moved, the position of the moved imaging element 21 can be easily detected by the imaging unit position detector. Therefore, the controller 31 can easily detect the relationship (relative position) between the position of the imaging element (imaging unit) 21 and the position of the culture vessel 7 on the basis of the position of the imaging element 21 detected by the imaging unit position detector.

Furthermore, in an eleventh modification, it is also possible to omit the movement mechanism 25, thus making the imaging device 3 stationary and making the glass plate 11, on which the culture vessel 7 is mounted, stationary as well, and to allow the user to manually move the position of the culture vessel 7 on the glass plate 11 while observing an image acquired by the imaging element 21.

From the above-described embodiments, the following aspects of the present disclosure are derived.

According to one aspect, the present disclosure provides an observation device including: an imaging unit configured to capture an image of a specimen contained in a vessel; an oblique illumination unit configured to perform an oblique illumination of the specimen from a plurality of illumination directions outside an optical axis of the imaging unit; a relative-position detector configured to detect a relationship between a position of the vessel and a position of the imaging unit; an illumination-direction switching unit configured to select a illumination direction to illuminate the specimen among the illumination directions of the oblique illumination unit on the basis of the relationship between the position of the vessel and the position of the imaging unit, which is detected by the relative-position detector; and an image processor configured to apply, on the basis of the illumination direction selected by the illumination-direction switching unit, image processing for reducing a shadow on the specimen caused by the oblique illumination, to an image of the specimen acquired by the imaging unit.

According to this aspect, the specimen contained in the vessel is subjected to oblique illumination by the oblique illumination unit and an image thereof is captured by the imaging unit. Furthermore, the illumination-direction switching unit selects illumination directions of the oblique illumination unit on the basis of the relationship between the position of the vessel and the position of the imaging unit, which is detected by the relative-position detector. Accordingly, it is possible to prevent illumination for the specimen from being blocked according to the position, the shape, etc., of the vessel and to efficiently apply oblique illumination to the specimen.

In this case, although a shadow on the specimen differs according to the illumination directions, and, when the directions of oblique illumination are switched, the shape of the specimen in the image changes, the image processor applies, on the basis of the illumination direction, processing for reducing the shadow on the specimen caused by oblique illumination to an image of specimen acquired by the imaging unit, thereby making it possible to suppress a change in the shape of the specimen between images in which the illumination directions differ. Therefore, it is possible to acquire an image from which a stable analysis result of the specimen can be obtained irrespective of the direction of oblique illumination.

In the above-described aspect, the relative-position detector may be provided with a stage on which the vessel is mounted, a stage movement mechanism configured to move the stage in at least a direction intersecting with the optical axis of the imaging unit, and a stage-position detector configured to detect the position of the stage on the basis of the amount of movement of the stage moved by the stage movement mechanism, wherein the relative-position detector may detect the relationship between the position of the vessel and the position of the imaging unit on the basis of the position of the stage detected by the stage-position detector.

With this configuration, the position of the stage can be easily found on the basis of the amount of movement thereof moved by the stage movement mechanism. Furthermore, the vessel is moved integrally with the stage. Therefore, the position of the vessel can be easily detected on the basis of the position of the stage detected by the stage-position detector. Accordingly, the relationship between the position of the imaging unit and the position of the vessel can be easily and accurately detected.

In the above-described aspect, the relative-position detector may be provided with a sensor configured to detect a mark made on the vessel; and the relative-position detector may detect the relationship between the position of the vessel and the position of the imaging unit on the basis of the mark detected by the sensor.

With this configuration, the entire vessel need not be detected, and the sensor can easily detect the position of the vessel merely by detecting the mark. Accordingly, the relationship between the position of the imaging unit and the position of the vessel can be easily and accurately detected.

In the above-described aspect, the relative-position detector may be provided with a camera configured to capture an image of the vessel and an image analyzer that analyzes an image acquired by the camera; and the relative-position detector may detect the relationship between the position of the vessel and the position of the imaging unit on the basis of an analysis result of the image obtained by the image analyzer.

With this configuration, the position of the vessel can be easily and accurately detected from information obtained when the image analyzer analyzes the image of the vessel. Accordingly, the relationship between the position of the imaging unit and the position of the vessel can be easily and accurately detected.

In the above-described aspect, the relative-position detector may be provided with a vessel placement part in which the vessel is placed and a sensor that senses a position with which the vessel is brought into contact in the vessel placement part, wherein the relative-position detector may detect the relationship between the position of the vessel and the position of the imaging unit on the basis of the position with which the vessel is brought into contact, which is sensed by the sensor.

With this configuration, the sensor merely senses the position on the vessel placement unit with which the vessel is brought into contact, thereby making it possible to easily and accurately detect the position of the vessel. Accordingly, the relationship between the position of the imaging unit and the position of the vessel can be easily and accurately detected.

In the above-described aspect, the relative-position detector may be provided with an imaging-unit movement mechanism on which the imaging unit is mounted and that can be moved in at least a direction intersecting with the optical axis of the imaging unit and an imaging-unit position detector that detects the position of the imaging unit on the basis of position information of the imaging-unit movement mechanism, wherein the relative-position detector may detect the relationship between the position of the vessel and the position of the imaging unit on the basis of the position of the imaging unit, which is detected by the imaging-unit position detector.

With this configuration, the imaging unit movement mechanism changes the position of the imaging unit in accordance with the position of the vessel and the position of the specimen in the vessel, thus making it possible to reliably capture an image of a desired part of the specimen. In this case, even when the imaging unit is moved, the position of the moved imaging unit can be easily detected by the imaging unit-position detector. Accordingly, the relationship between the position of the imaging unit and the position of the vessel can be easily and accurately detected.

In the above-described aspect, the oblique illumination unit may be provided with: a plurality of light sources whose light intensities can be changed independently; and a light-intensity adjuster that adjusts the light intensities of the plurality of light sources.

With this configuration, the light-intensity adjuster changes the light intensities of the respective light sources separately, thus making it possible to apply oblique illumination to the specimen by means of a desired one or some of the light sources according to the position and the shape of the vessel.

In the above-described aspect, the light-intensity adjuster may switch on and off of states the plurality of light sources.

With this configuration, it is possible to avoid oblique illumination from an undesired direction and to apply oblique illumination to the specimen only from a desired direction.

In the above-described aspect, the plurality of light sources may be arranged along a ring around the optical axis of the imaging unit.

With this configuration, the positions, in the circumferential direction, of the light sources that are made to perform illumination are switched, thereby making it possible to capture images of the specimen illuminated from directions different in the circumferential direction.

In the above-described aspect, the plurality of light sources may be disposed, around the imaging unit, at positions whose distances to the optical axis of the imaging unit are different from each other.

With this configuration, the positions, in the radial direction, of the light sources that are made to perform illumination are switched, thereby making it possible to capture images of the specimen illuminated from angles different in the direction along the optical axis of the imaging unit. Specifically, the specimen can be subjected to oblique illumination at a small angle with respect to the optical axis of the imaging unit from the light source that is disposed at a position close to the optical axis of the imaging unit in the radial direction, whereas the specimen can be subjected to oblique illumination at a large angle with respect to the optical axis of the imaging unit from the light source that is disposed at a position away from the optical axis of the imaging unit in the radial direction.

In the above-described aspect, the oblique illumination unit may be provided with: a light source that can be moved in a direction intersecting with the optical axis of the imaging unit; and a light-source movement mechanism that moves the light source.

With this configuration, the light-source movement mechanism changes the position of the light source, thereby making it possible to switch illumination directions, with a small number of light sources, and to subject the specimen to oblique illumination.

In the above-described aspect, the image processor may apply a multiplication to an image of the specimen by using gain values on the basis of a gain map that is composed of gain values that are smaller on a nearer side and are larger on a farther side along the illumination direction with respect to the specimen.

With this configuration, it is possible to suppress shading that is caused on the image according to the illumination direction.

In the above-described aspect, the image processor may apply a Fourier transform to the image of the specimen, multiplies, by −1, a region of the image that has been subjected to the Fourier transform, the region including frequency components of shadows, among frequencies along the illumination direction with respect to the specimen, and then applies an inverse Fourier transform thereto.

With this configuration, it is possible to shift the phases of frequencies along the illumination direction in the image of the specimen. In this case, high-frequency components for the edges etc. of the specimen change little in appearance, thus remaining the same, and medium-frequency components for the shadow etc. of the specimen change a lot in appearance, thus decreasing. Therefore, it is possible to efficiently reduce the shadow on the specimen, which is caused by oblique illumination.

In the above-described aspect, the image processor may apply a high-pass filter to the image that has been subjected to the Fourier transform.

With this configuration, it is possible to remove low-frequency components for portions where color changes less, other than the edges of the specimen and the shadows on the specimen, in the image that has been subjected to the Fourier transform. Accordingly, a partial region of the image that has been subjected to the Fourier transform is multiplied by −1, thereby making it possible to reduce a striped pattern caused at the low-frequency components, thus improving the image quality.

According to a second aspect, the present disclosure provides an observation method comprising: a switching step of selecting a illumination direction to apply oblique illumination to a specimen among illumination directions on the basis of a relationship between a position of a vessel that contains the specimen and a position of an imaging unit that captures an image of the specimen in the vessel; an illumination step of applying the oblique illumination to the specimen from the illumination direction selected in the switching step; an image-capturing step of capturing, by means of an imaging unit, an image of the specimen to which the oblique illumination is applied by the illumination step; and an image processing step of applying, on the basis of the illumination direction selected by the switching step, image processing for reducing a shadow on the specimen caused by the oblique illumination, to an image of the specimen acquired by the imaging unit.

According to this aspect, the specimen is subjected to oblique illumination in the illumination step from the illumination direction of oblique illumination selected in the switching step on the basis of the relationship between the position of the vessel and the position of the imaging unit, and an image of the specimen is captured in the image-capturing step. Accordingly, it is possible to prevent illumination for the specimen from being blocked according to the position, the shape, etc., of the vessel and to efficiently apply oblique illumination to the specimen.

In this case, processing for reducing the shadow on the specimen caused by oblique illumination is applied, in the image processing step, to the image of the specimen acquired in the image-capturing step, on the basis of the illumination direction, thereby making it possible to suppress a change in the shape of the specimen between images in which the illumination directions differ. Therefore, it is possible to acquire an image from which a stable analysis result of the specimen can be obtained irrespective of the direction of oblique illumination.

According to the aforementioned aspects, an advantageous effect is afforded in that it is possible to acquire an image from which a stable analysis result of a specimen can be obtained irrespective of the direction of oblique illumination.

REFERENCE SIGNS LIST

1 observation device
7 culture vessel (vessel)
21 imaging element (imaging unit)
23 oblique illumination device (oblique illumination unit)
31 controller (relative-position detector, illumination-direction switching unit, light-intensity adjuster)
35 image processor
S1 switching step
S2 illumination step
S3 image capturing step
S4 image processing step

The invention claimed is:

1. An observation device comprising:
   an imaging unit configured to capture an image of a specimen contained in a vessel;
   an oblique illumination unit configured to perform an oblique illumination of the specimen from a plurality of illumination directions outside an optical axis of the imaging unit;
   a relative-position detector configured to detect a relationship between a position of the vessel and a position of the imaging unit;
   an illumination-direction switching unit configured to select a illumination direction to illuminate the specimen among the illumination directions of the oblique illumination unit on the basis of the relationship between the position of the vessel and the position of the imaging unit, which is detected by the relative-position detector; and
   an image processor configured to apply, on the basis of the illumination direction selected by the illumination-direction switching unit, image processing for reducing a shadow on the specimen caused by the oblique illumination, to an image of the specimen acquired by the imaging unit.

2. An observation device according to claim 1, wherein the relative-position detector is provided with a stage on which the vessel is mounted, a stage movement mechanism configured to move the stage in at least a direction intersecting with the optical axis of the imaging unit, and a stage-position detector configured to detect the position of the stage on the basis of the amount of movement of the stage moved by the stage movement mechanism,
   wherein the relative-position detector detects the relationship between the position of the vessel and the position of the imaging unit on the basis of the position of the stage detected by the stage-position detector.

3. An observation device according to claim 1, wherein the relative-position detector is provided with a sensor configured to detect a mark made on the vessel; and the relative-position detector detects the relationship between the position of the vessel and the position of the imaging unit on the basis of the mark detected by the sensor.

4. An observation device according to claim 1, wherein the relative-position detector is provided with a camera configured to capture an image of the vessel and an image analyzer that analyzes an image acquired by the camera; and the relative-position detector detects the relationship between the position of the vessel and the position of the imaging unit on the basis of an analysis result of the image obtained by the image analyzer.

5. An observation device according to claim 1, wherein the relative-position detector is provided with a vessel placement part in which the vessel is placed and a sensor that senses a position with which the vessel is brought into contact in the vessel placement part,
   wherein the relative-position detector detects the relationship between the position of the vessel and the position of the imaging unit on the basis of the position with which the vessel is brought into contact, which is sensed by the sensor.

6. An observation device according to claim 1, wherein the relative-position detector is provided with an imaging-unit movement mechanism on which the imaging unit is mounted and that can be moved in at least a direction intersecting with the optical axis of the imaging unit and an imaging-unit position detector that detects the position of the imaging unit on the basis of position information of the imaging-unit movement mechanism,
  wherein the relative-position detector detects the relationship between the position of the vessel and the position of the imaging unit on the basis of the position of the imaging unit, which is detected by the imaging-unit position detector.

7. An observation device according to claim 1, wherein the oblique illumination unit is provided with: a plurality of light sources whose light intensities can be changed independently; and a light-intensity adjuster that adjusts the light intensities of the plurality of light sources.

8. An observation device according to claim 7, wherein the light-intensity adjuster switches on and off of the plurality of light sources.

9. An observation device according to claim 7, wherein the plurality of light sources are arranged along a ring around the optical axis of the imaging unit.

10. An observation device according to claim 7, wherein the plurality of light sources are disposed, around the imaging unit, at positions whose distances to the optical axis of the imaging unit are different from each other.

11. An observation device according to claim 1, wherein the oblique illumination unit is provided with: a light source that can be moved in a direction intersecting with the optical axis of the imaging unit; and a light-source movement mechanism that moves the light source.

12. An observation device according to claim 1, wherein the image processor applies a multiplication to an image of the specimen by using gain values on the basis of a gain map that is composed of gain values that are smaller on a nearer side and are larger on a farther side along the illumination direction with respect to the specimen.

13. An observation device according to claim 1, wherein the image processor applies a Fourier transform to the image of the specimen, multiplies, by −1, a region of the image that has been subjected to the Fourier transform, the region including frequency components of shadows, among frequencies along the illumination direction with respect to the specimen, and then applies an inverse Fourier transform thereto.

14. An observation device according to claim 13, wherein the image processor applies a high-pass filter to the image that has been subjected to the Fourier transform.

15. An observation method comprising:
  a switching step of selecting a illumination direction to apply oblique illumination to a specimen among illumination directions on the basis of a relationship between a position of a vessel that contains the specimen and a position of an imaging unit that captures an image of the specimen in the vessel;
  an illumination step of applying the oblique illumination to the specimen from the illumination direction selected in the switching step;
  an image-capturing step of capturing, by means of an imaging unit, an image of the specimen to which the oblique illumination is applied by the illumination step; and
  an image processing step of applying, on the basis of the illumination direction selected by the switching step, image processing for reducing a shadow on the specimen caused by the oblique illumination, to an image of the specimen acquired by the imaging unit.

* * * * *